United States Patent
Islam et al.

(10) Patent No.: US 9,395,400 B1
(45) Date of Patent: Jul. 19, 2016

(54) TEST FIXTURE TO TEST DEVICE CONNECTORS

(71) Applicant: Amazon Technologies, Inc., Reno, NV (US)

(72) Inventors: Rashed Adnan Islam, San Jose, CA (US); Saket Patil, Sunnyvale, CA (US); Ian Charles Rust, Palo Alto, CA (US)

(73) Assignee: Amazon Technologies, Inc., Seattle, WA (US)

( * ) Notice: Subject to any disclaimer, the term of this patent is extended or adjusted under 35 U.S.C. 154(b) by 477 days.

(21) Appl. No.: 13/794,172

(22) Filed: Mar. 11, 2013

(51) Int. Cl.
*G01R 31/04* (2006.01)
*G01R 31/02* (2006.01)
*G01N 3/48* (2006.01)

(52) U.S. Cl.
CPC ........ *G01R 31/04* (2013.01); *G01N 3/48* (2013.01); *G01R 31/025* (2013.01); *G01R 31/026* (2013.01); *G01R 31/041* (2013.01)

(58) Field of Classification Search
CPC ......... G01N 3/48; G01R 31/04; G01R 31/041
USPC .......................................................... 324/538
See application file for complete search history.

(56) References Cited

U.S. PATENT DOCUMENTS

| | | | | |
|---|---|---|---|---|
| 880,991 A * | 3/1908 | Von Hassel | ............... | G01N 3/48 73/82 |
| 2,158,630 A * | 5/1939 | Lloyd | ................... | H04M 3/22 324/538 |
| 2,188,898 A * | 2/1940 | Haskell | .................. | G01N 3/30 73/12.09 |
| 2,359,044 A * | 9/1944 | MacBride | ................ | G01N 3/30 73/12.14 |
| 2,362,589 A * | 11/1944 | Simmons, Jr. | ........... | G01N 3/30 73/12.14 |
| 2,381,723 A * | 8/1945 | Crist | ...................... | B65G 67/00 414/361 |
| 3,285,060 A * | 11/1966 | Pessen | ..................... | G01N 3/30 73/12.14 |
| 3,590,631 A * | 7/1971 | Gonze | ...................... | G01N 3/16 73/794 |
| 4,113,200 A * | 9/1978 | Tanaka | .................... | B60R 22/44 242/372 |
| 4,270,383 A * | 6/1981 | Singer | .................... | G01N 3/307 73/82 |
| 4,425,786 A * | 1/1984 | Sirkkola | .................. | G01N 3/30 73/12.14 |
| 4,442,697 A * | 4/1984 | Jones | ....................... | G01N 3/30 73/12.14 |

(Continued)

OTHER PUBLICATIONS

Zhou, C.Y. ; Yu, T.X. ; Lee, R.S.W.; Design of shock table tests to mimic real-life drop conditions for portable electronic device; Published in: International Conference on Electronic Materials and Packaging, 2006. EMAP 2006.; Date of Conference: Dec. 11-14, 2006; pp. 1-5.*

(Continued)

*Primary Examiner* — Jermele M Hollington
*Assistant Examiner* — Christopher McAndrew
(74) *Attorney, Agent, or Firm* — Lee & Hayes, PLLC

(57) ABSTRACT

This disclosure is directed to a test fixture to test a robustness of a connection port of an electronic device, a cable connector coupled to the connection port, or both. The test fixture may enable repeatable testing using predetermined test parameters. The test fixture may secure the electronic device using a clamp. A pendulum may be mounted in the test fixture and rotatable to cause an impact of a weight against a cable connector coupled to the connection port of an electronic device. After the impact, the integrity and/or functionality of the cable connector, the connection port, or both may be inspected. In accordance with one or more embodiments, the test fixture may be under at least partial control of a controller. The controller may enable creation or control of test parameters, repeat testing, cycle testing, and/or inspection (e.g., determining whether the connection is maintained and/or functional, etc.).

24 Claims, 11 Drawing Sheets

(56) References Cited

U.S. PATENT DOCUMENTS

| | | | | | |
|---|---|---|---|---|---|
| 4,543,523 | A | * | 9/1985 | Moran | G01R 31/02 324/538 |
| 4,556,177 | A | * | 12/1985 | Kuwakado | B60R 22/40 242/384.4 |
| 5,440,235 | A | * | 8/1995 | Oko | H01R 13/443 174/138 F |
| 5,471,868 | A | * | 12/1995 | Nolan | G01N 3/48 73/81 |
| 5,623,199 | A | * | 4/1997 | Taniguchi | G01R 31/04 324/538 |
| 5,689,191 | A | * | 11/1997 | Kashiyama | H01R 43/22 324/538 |
| 5,701,079 | A | * | 12/1997 | Yagi | G01R 31/045 324/538 |
| 5,712,569 | A | * | 1/1998 | Canu | G01R 31/045 324/538 |
| 5,712,570 | A | * | 1/1998 | Heo | G01R 31/2853 324/537 |
| 5,744,966 | A | * | 4/1998 | Sato | G01R 31/04 29/593 |
| 5,777,480 | A | * | 7/1998 | Hatagishi | G01R 31/04 324/538 |
| 6,435,001 | B1 | * | 8/2002 | Song | G01M 7/08 73/12.04 |
| 6,837,094 | B2 | * | 1/2005 | Pringle | A63B 59/0074 73/12.02 |
| 7,360,393 | B1 | * | 4/2008 | Abke | G01M 7/08 73/12.14 |
| 8,272,247 | B2 | * | 9/2012 | Kojovic | B02C 19/0025 73/12.05 |
| 2004/0103713 | A1 | * | 6/2004 | Voon | G01N 3/48 73/12.04 |
| 2004/0182131 | A1 | * | 9/2004 | Pringle | A63B 59/0074 73/12.09 |
| 2005/0016256 | A1 | * | 1/2005 | Ishikawa | G01N 3/303 73/12.13 |
| 2005/0188744 | A1 | * | 9/2005 | Camio | G01M 7/08 73/12.01 |
| 2005/0189710 | A1 | * | 9/2005 | Gemma | B65H 5/06 271/265.01 |
| 2009/0199625 | A1 | * | 8/2009 | Kojovic | B02C 19/0025 73/82 |
| 2009/0322554 | A1 | * | 12/2009 | Hernandez-Marti | G01R 31/021 340/854.9 |

OTHER PUBLICATIONS

Brochure Dated Dec. 7, 2009 to Qualitest.*
P. Melnyk, I.J. Toth; Development of Impact Resistant Boron/Aluminum Compositesturbojet Engine Fan Blades, National Aeronautics and Space Administration NASA Lewis Research Center, May 1975.*
Highlighted Brochure Dated Dec. 7, 2009 to Qualitest.*
C.Y. Zhou, T.X. Yu and Ricky S.W. Lee; Design of Shock table tests to mimic real-life drop conditions for portable electronic device; International Conference on Electronic Materials and Packaging, 2006. EMAP 2006. IEEE, Dec. 11-14, 2006; pp. 1-5).*
Jennifer Markarian; Mechanical testing suppliers strive for accuracy and reproducibility, Plastics, Additives and Compounding; vol. 11, Issue 3, May-Jun. 2009, pp. 18-22.*

* cited by examiner

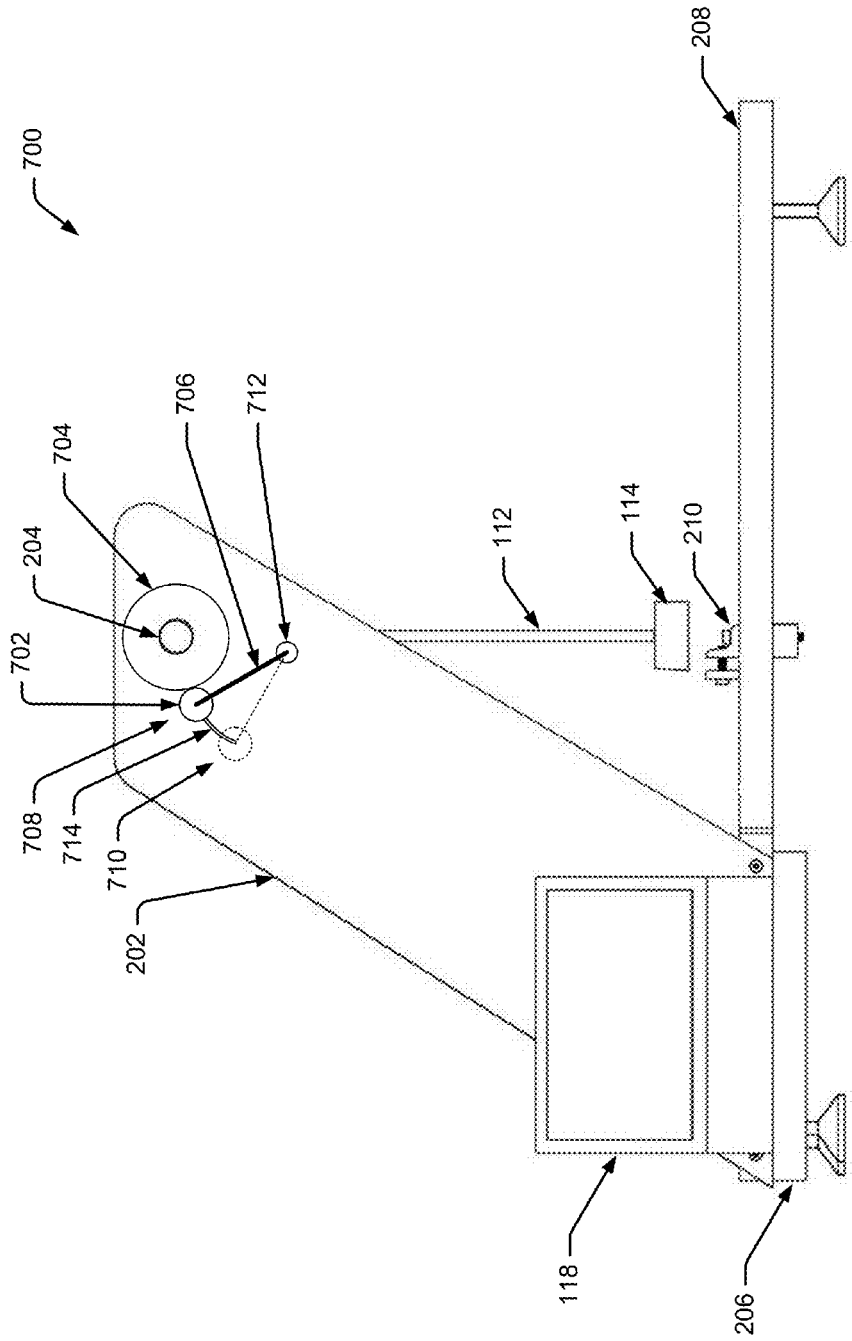

US 9,395,400 B1

TEST FIXTURE TO TEST DEVICE CONNECTORS

BACKGROUND

Electronic devices have become commonplace in almost every environment. For example, mobile telephones, laptop computers, tablet computers, portable music players, portable gaming devices, and other portable electronic devices are commonly used for work, pleasure, or both, and accompany people in many daily activities. For example, people often travel with electronic devices, bring these devices to school, and use these devices in public places. During use, the electronic devices are often subjected to regular wear, including at times, impacts with other objects or surfaces (e.g., drops by user, etc.), which may result in a compromise of functionality of one or more features of the electronic devices or a compromise in an appearance of the electronic devices.

Many electronic devices include connection ports that are connected to cable connectors. For example, an electronic device may include one or more connection ports to accommodate a power supply, an audio input/output, a video input/output, and/or a data input/output (e.g., a universal serial bus (USB), etc.). Like the electronic device itself, the connection ports and/or the cable connectors may be subjected to wear, including impacts with other objects or surfaces and/or improper or accidental cable separation (e.g., cable pulled out of the electric device when a person trips over the cable, etc.). The wear and/or impacts may result in decreased operation of the connection ports and/or the cable connectors, such as by terminating operation, creating intermittent operations, or diminishing functionality of the operation (e.g., slower throughput, increased difficulty in making a connection, etc.).

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

FIG. 7 is side elevation view of the illustrative test fixture that includes a drive motor configured to reposition a pendulum prior to a test.

DETAILED DESCRIPTION

This disclosure is directed, in part, to a test fixture to test a robustness of a connection port of an electronic device, a cable connector coupled to the connection port, or both the connection port and the cable connector. The test fixture may enable repeatable testing using predetermined test parameters. The test fixture may secure the electronic device using a clamp. A pendulum may be mounted in the test fixture and rotatable to cause an impact of a weight against a cable connector coupled to the connection port of an electronic device. After the impact, the integrity and/or functionality of the cable connector, the connection port, or both may be inspected.

In accordance with one or more embodiments, the test fixture may be under at least partial control of a controller. The controller may be implemented as one or more of a switch, a simple processor, a complex processor, or a stand-alone computing device. The controller may enable creation or control of test parameters, repeat testing, cycle testing, and/or inspection (e.g., determining whether the connection is maintained and/or functional, etc.).

The test fixture may employ one or more motors, actuators, magnets, and/or other devices or mechanisms that the controller uses to cause the testing device to perform various actions. For example, the controller may selectively power a motor that resets the pendulum to a drop position. As another example, the controller may calculate the drop position based on data input by a user (e.g., based in part on the weight of the electronic device, etc.). The drop position, when combined with a known weight (which may be selectable), may enable determination of benchmark data such as a test velocity of the weight, a test momentum and energy of the weight, and so forth at a point in time just prior to impact of the weight and the cable connector.

The apparatuses, techniques and systems described herein may be implemented in a number of ways. Example implementations are provided below with reference to the following figures.

Figure 1:
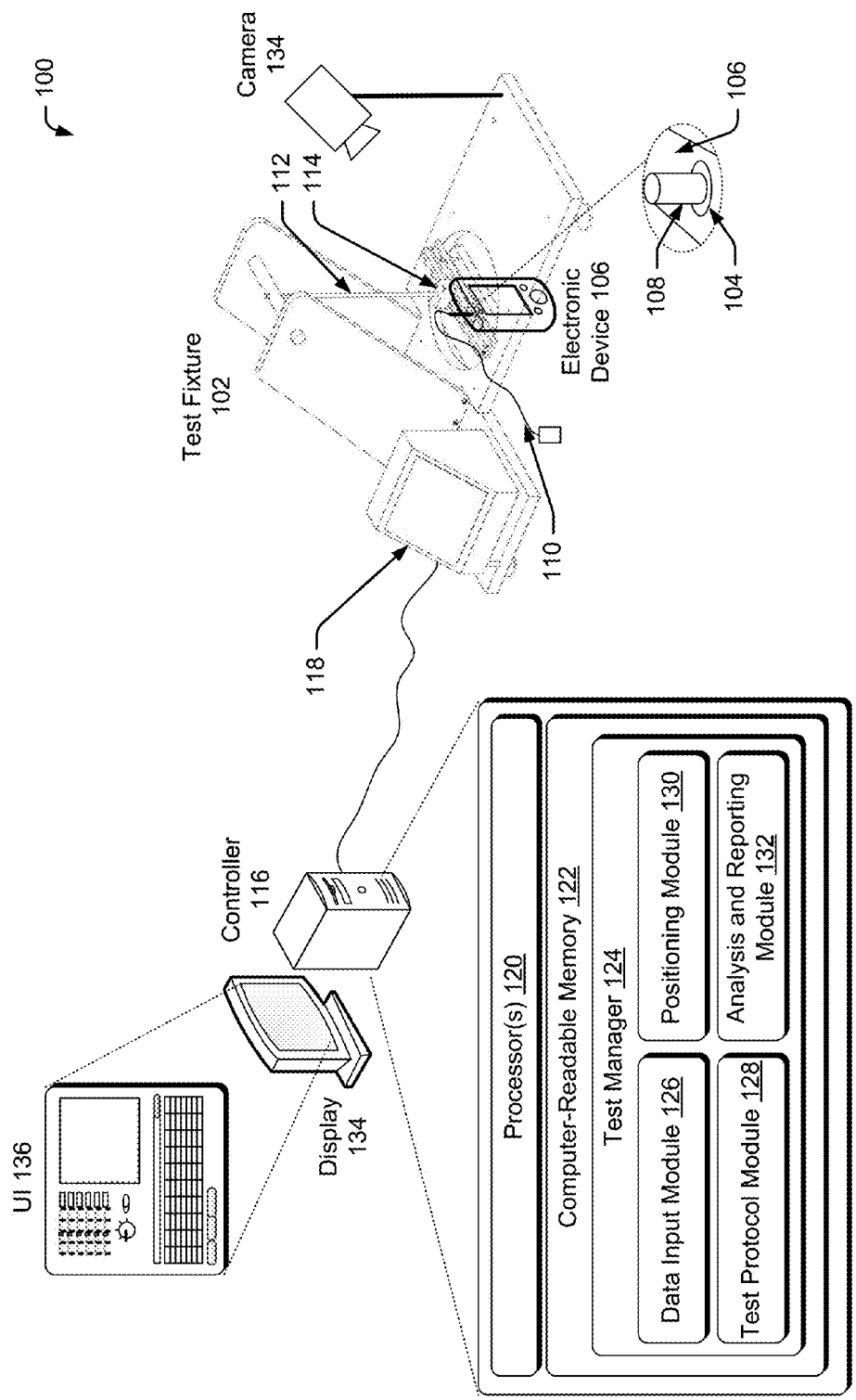
FIG. 1 is a schematic diagram of an illustrative environment that includes a test fixture to test device connectors and a controller that interacts with the test fixture.

FIG. 1 is a schematic diagram of an illustrative environment 100. The environment 100 may include a test fixture 102 to test a connection port 104 of an electronic device 106, a cable connector 108 coupled to the connection port 104, or both the connection port 104 and the cable connector 108. The test may determine a strength, durability, toughness, robustness, sturdiness, and/or heftiness of the connection port 104, the cable connector 108, or both. The cable connector 108 may be coupled to an end of a cable 110. The cable 110 may have a functionality, such as to transmit power, transmit data, transmit audio, transmit video, and/or a combination thereof.

To perform the test, the test fixture 102 may enable a pendulum 112 to move from a first position (or first angle) to a second position (or second angle), at which a weight 114 coupled to the pendulum 112 impacts the cable connector 108. The impact may be proximate the connection port 104 or a predetermined distance from the connection port 104 (e.g., further up the cable 110 connected to the cable connector 108). For example, a test may simulate a person tripping over the cable 110 attached to the electronic device 106. The second position may be a lowest point of travel of the weight 114 of the pendulum 112 (i.e., where the pendulum 112 and the weight 114 have no potential energy when released at the second position). The pendulum 112 and the weight 114 have potential energy at the first position. The test fixture 102 may include a trigger mechanism to restrain the pendulum 112 and to release of the pendulum. Various trigger mechanisms are discussed below. In some embodiments, the test fixture 102 may include one or more motors, actuators, magnets, and/or other devices or mechanisms that a controller 116 uses to cause the test fixture 102 to perform various actions. The actions may include movement or positioning of the electronic device 106, movement of the pendulum 112, movement of the trigger mechanism, and/or other movements or actions. For example, the controller 116 may selectively power a motor that repositions the pendulum 112 to the first position after a test has been performed. The controller 116 may calculate a location or angle of the first position based on data input by a user or based on other data (e.g., based in part on the weight of the electronic device 106, etc.). The drop position, when combined with a known weight (which may be adjustable/replaceable), may enable determination of a velocity of the weight 114 just prior to impact of the weight 114 and the cable connector 108. The velocity may be confirmed and/or determined by a sensor, such as a motion sensor, a camera, or other types of sensors. As another example, the controller 116 may adjust a magnetic field of a magnet that restrains the pendulum 112 in the first position to initiate movement of the weight 114 towards the cable connector 108. The magnetic field may be adjusted by controlling a current to an electromagnet, physically moving a magnet, or by other known techniques to adjust a magnetic field.

In accordance with one or more embodiments, the controller 116 may be implemented as one or more of a switch, a simple processor, a complex processor, or a stand-alone computing device. In the environment 100, the controller 116 is shown as a stand-alone computing device that is in communication with the test fixture 102 via an integrated controller 118. However, the integrated controller 118 may house some or all of the components of the controller 116, such as by including switches, a display screen, and so forth. The integrated controller 118 may include connections to various motors, actuators, etc. Thus, the integrated controller 118 may include similar components as described below for the controller 116, or the integrated controller 118 may be limited to including a connection to connect the controller 116 to the various motors, actuators, etc. included in the test fixture 102.

The controller 116 may include one or more processors 120 and computer-readable memory 122. The computer-readable media 122 may store various modules, applications, programs, or other data. The computer-readable media 122 may include instructions that, when executed by the processor(s) 120, cause the processor(s) to perform the operations described herein for the test fixture 102. The computer-readable media 122 may store a test manager 124 that includes the instructions to perform the operations. The test manager 124 may include a data input module 126, a test protocol module 128, a positioning module 130, and/or an analysis and reporting module 132. Each module is discussed in turn.

The data input module 126 may enable a user to input data about the electronic device 106, the test parameters, and/or other inputs. In some embodiments, the data input module 126 may include connectivity to the cable 110 to enable determination of whether the cable can perform an intended functionality following an impact of the weight and the cable connector 108 (e.g., determine whether the cable 110 can still exchange data/power with the electronic device, etc.).

The test protocol module 128 may create and implement a test. For example, the test may include one or more cycles where each cycle includes a release of the pendulum 112 from the first position and an impact of the weight 114 against the cable connector 108 at the second position. The cycle may also include repositioning of the pendulum 112 to the first position, movement and/or repositioning of the electronic device 106, and/or other operations.

The positioning module 130 may position the electronic device 106, the pendulum 112, and/or other movable components of the test fixture 102. For example the pendulum 112 may be positioned at different angles (or distances from the cable connector 108), which may result in different velocities of the weight 114 immediately prior to impact with the cable connector 108. The selected angle for the first position may be one of the test parameters which may be selected by a user and/or computed by the controller 116 based on other information (e.g., the weight of the electronic device 106, a distance of a drop test, and/or other information). The positioning module 130 may also move and/or rotate the electronic device 106 to position the cable connector 108 in a path of travel of the weigh 114. The electronic device 106 may be secured in a clamp that can be rotate about one or more axes and/or translate along two or more axes.

The analysis and reporting (AR) module 132 may perform analysis of the results of one or more cycles of a test. The AR module 132 may analyze information, such as imagery from a camera 134 showing results of an impact of the weight 114 and the cable connector 108. The information may include a functionality of the cable connector 108 and/or the connection port 104. The information may include indicia of an integrity of the cable connector 108 and/or the connection port 104 (e.g., changes to an appearance of these parts). The AR module may report results from the analysis, which may be visible via a display 134 that presents a user interface (UI) 136. For example, the report may include a number of test cycles performed prior to failure of the functionality and/or a loss of integrity. The functionality may include full functionality, intermittent functionality, degraded functionality, and no functionality (e.g., slower throughput, increased difficulty in making a connection, etc.). In some instances, the functionality may be determined by testing the cable connector 108 and/or the connection port 104 individually. The integrity may be determined by inspecting the cable connection 108 and/or the connection port 104 for fractures, cracks, blemishes, and/or other indicia of breakage.

Figure 2:
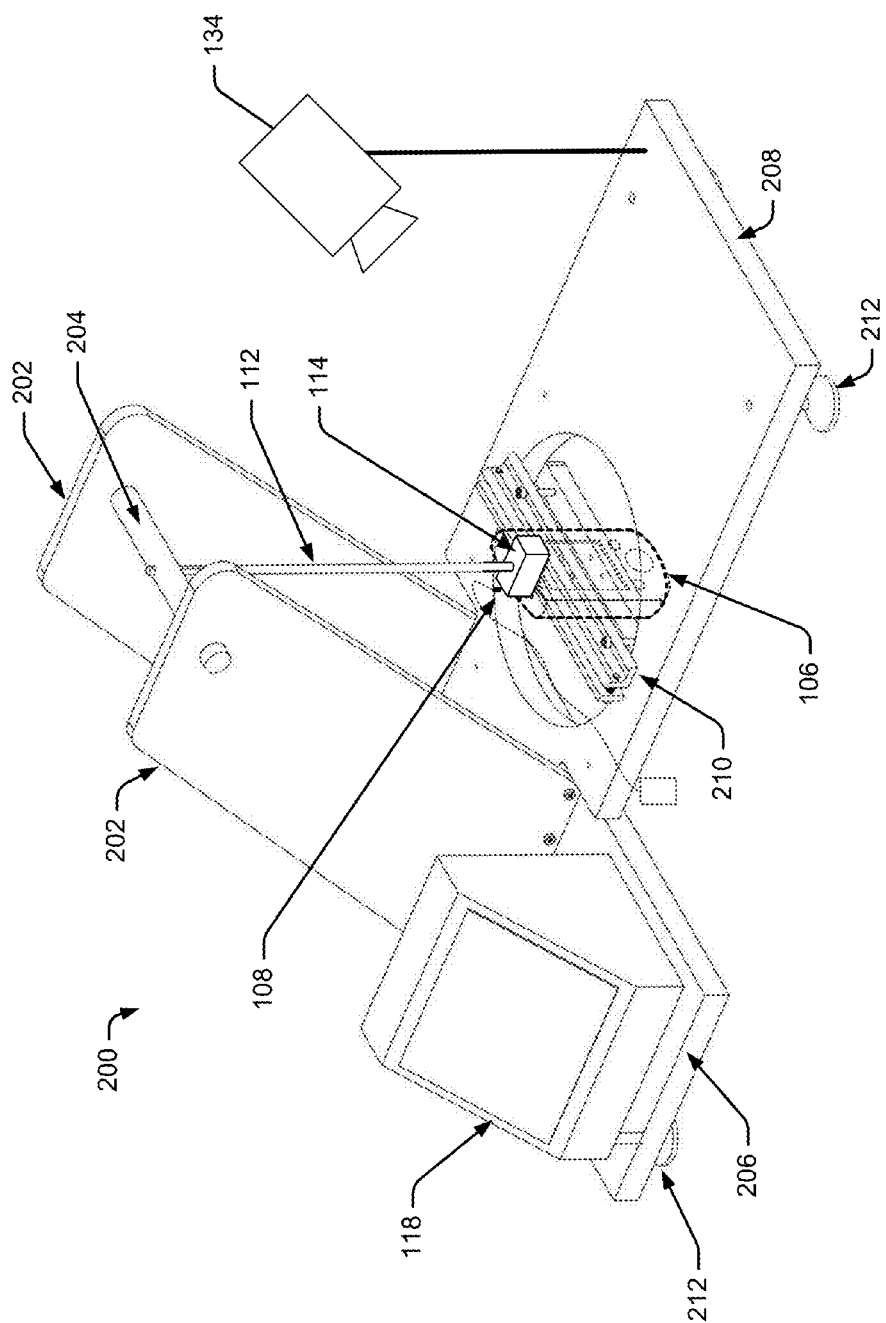
FIG. 2 is an isometric view of an illustrative test fixture to test device connectors.

FIG. 2 is an isometric view of an illustrative test fixture 200 to test device connectors. The test fixture 200 may be the same as the test fixture 102 or may include some differences. However, the basic operation of the test fixture 200 is similar to the described operation of the test fixture 102. The electronic device 106, the cable connector 108, and the cable 110 are shown in dashed lines in this figure and in other figures to indicate that these apparatuses are not part of the test fixture 200, but instead the test fixture 200 is used to perform tests on these apparatuses as explained herein.

The test fixture 200 may include one or more support arms 202 that secure and position an axle 204 in an elevated location relative to a platform 206 that supports the arms 202. The axle 204 may be secured and positioned at or near a distal end of the arms 202. The axle 204 may be coupled to the pendulum 112. The weight 114 may be located on a distal end of the pendulum 112 opposite the axle 204. In some embodiments, the axle 204 may include bearings to enable rotation of the axle, with respect to the arms 202, with minimal friction. The axle 204 enables the pendulum 112 to swing from a first position to a second position, as described above.

The test fixture 200 may include a base 208 that supports a clamp 210. The base may be coupled to the arms 202 or the platform 206. The clamp 210 may be used to secure the electronic device 102 in a fixed position. The clamp 210 and/or the base 208 may be moveable to position the cable connector 108 in a path of travel of the weight 114. In some embodiments, the base 208 may translate relative to the platform 206, to enable movement of the clamp along two or more axes, as described with reference to FIG. 5. The clamp 210 may be used to secure many types of electronic devices having various shapes, including curved surfaces. The electronic devices may be mobile telephones, table computers, electronic book (eBook) reader devices, music players, game consoles, laptop computers, and/or other types of electronic devices that include one or more connection ports (e.g., the connection port 104) that engage one or more cable connectors (e.g., the cable connector 108). The cable connector may couple with the connection port via a male/female coupling, a magnetic coupling, friction coupling, and/or other types of couplings. For example, the cable connector may include a housing that is inserted into the connection port, and when inserted, the cable connector may engage one or more contacts that enable transmission of power, data, audio, video, etc. The base 208 and/or the platform 206 may include feet 212. The feet may be adjustable to level the test fixture 200. Further detail about the feet 212 is provided with reference to FIG. 6B. The feet 212 may be long enough to enable clearance of the electronic device 106 from a table or other surface.

The test fixture 200 may include one or more cameras (e.g., the camera 134). The cameras may record still images and/or moving images. The cameras may record an impact of the weight 114 and the cable connector 108. The images may be used to measure a deflection of the cable connector 108 relative the electronic device 106 and/or fractures (or lack thereof) of the cable connector 108 and/or the connection port 104. The camera(s) may be repositioned, possibly under control of the integrated controller 118. The cameras may be activated to record only a portion of the events of the operation of the test fixture 200, such as the events during or immediately following the impact of the weight 114 and the cable connection 108. For example, the integrated controller 118 may activate the camera after releasing the pendulum and then deactivate the camera after the impact.

The integrated controller 118 may include some or all of the hardware of the controller 116, which may be wholly or partially integrated in the test fixture 118. For example, a simple implementation of the integrated controller 118 may include a switch to trigger a release of the pendulum 112 from the first position.

Figure 3:
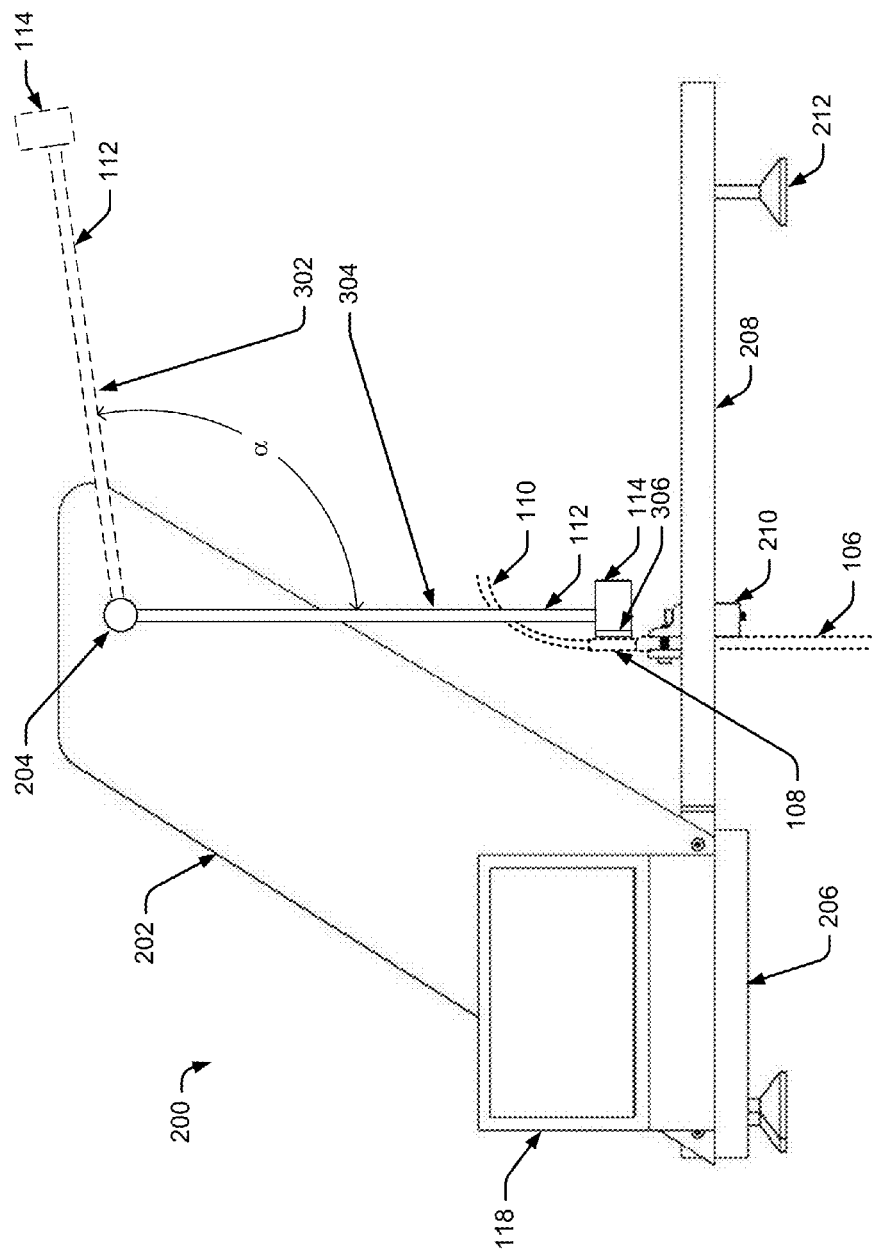
FIG. 3 is a side elevation view of the illustrative test fixture to test device connectors.

FIG. 3 is a side elevation view of the illustrative test fixture 200 to test device connectors. As shown in FIG. 3, the pendulum 112 and the weight 114 may rotate and move from a first position 302 (where the pendulum 112 and the weight 114 are shown with dashed lines) to a second position 304 (where the pendulum 112 and the weight 114 are shown with solid lines). The second position 304 may be a lowest point of travel of the weight 114 of the pendulum 112 (i.e., where the pendulum 112 and the weight 114 have no potential energy when released at the second position 304). The pendulum 112 and the weight 114 have potential energy at the first position 302. The first position 302 may be selected such that the weigh 114 has desired amount of potential energy that translates to a desired velocity at a point immediate prior to impact of the weight 114 and the cable connector 108. The first position 302 may have a first angle α measured from the second position 304. The second position 304 may have a second angle α, which may be at zero degrees (measured relative to a line parallel to the pendulum in the second position). The selection of the first position 302 may vary depending on the test parameters (desired velocity prior to impact, etc.).

In some embodiments, the weight 114 may include a load cell 306 that may be used to measure information associated with an impact between the weight 114 and the cable connector 108. The load cell 306 may provide data that is received and analyzed by the analysis and reporting module 132 of the controller 116 (or the integrated controller 118). In some embodiments, the weight 114 may include other motion detection devices, such as an accelerometer.

Figure 4:
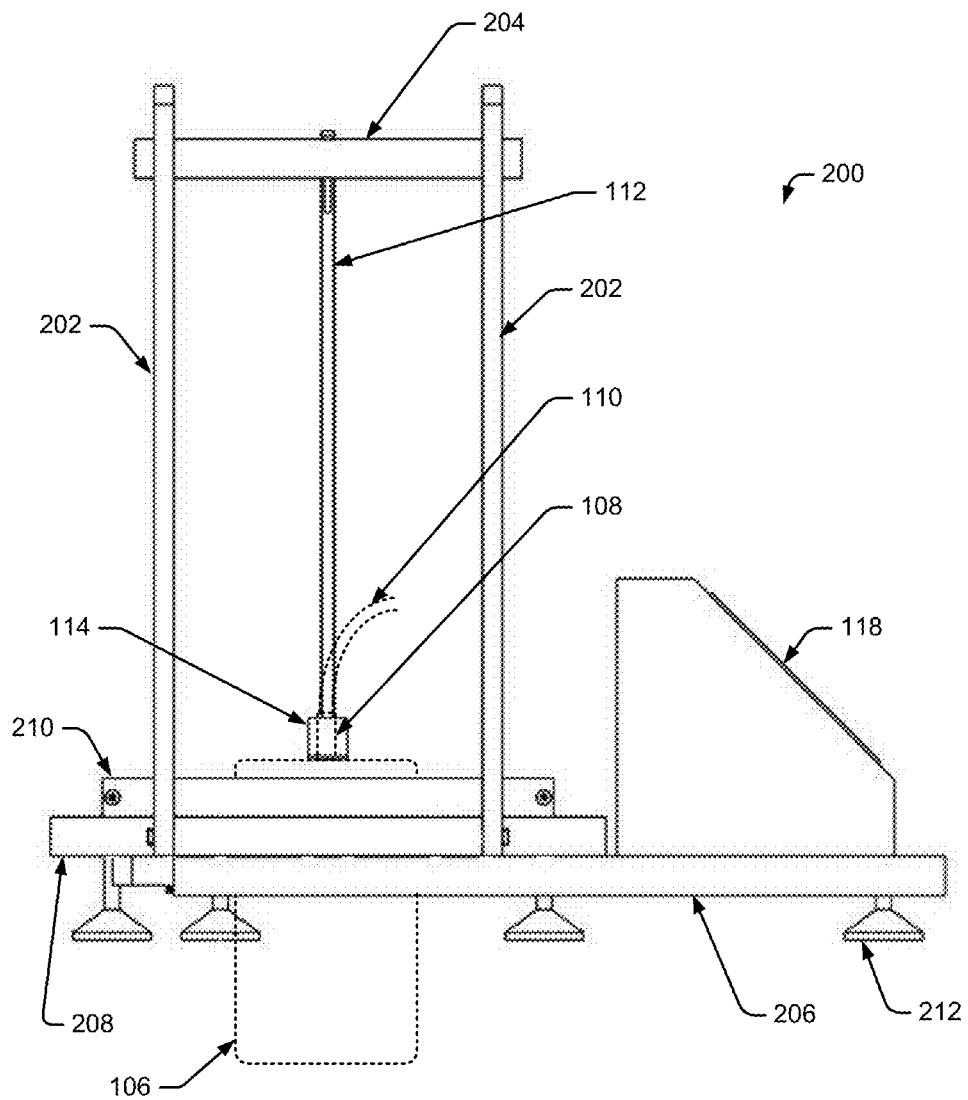
FIG. 4 is a front elevation view of the illustrative test fixture to test device connectors.

FIG. 4 is a front elevation view of the illustrative test fixture 200 to test device connectors. As shown in FIG. 4, the electronic device 106 is positioned by the clamp 210 to locate the cable connector 108 in a path of travel of the weight 114 such that the weigh 114 impacts the cable connector 108 after the pendulum 112 is released from the first position 302 (as shown in FIG. 3).

Figure 5:
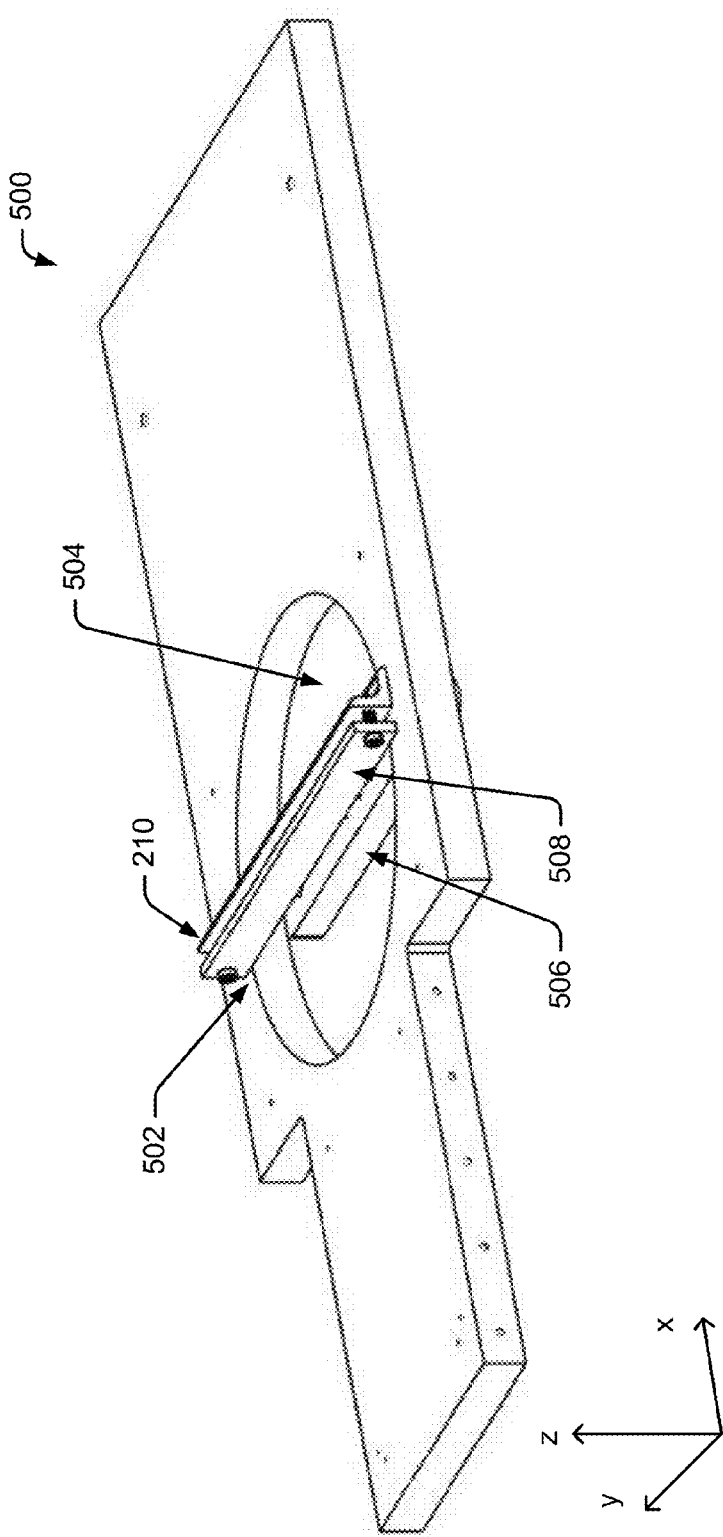
FIG. 5 is an isometric view of an illustrative base of the test fixture, the base used to secure a device that includes at least one connection port that is coupled to a cable connector.

FIG. 5 is an isometric view of an illustrative base 500 of the test fixture 102. The base 500 may be the same or different than the base 208 described above. The base 500 may be used to secure and position the clamp 210. In some embodiments, the clamp 210 may be coupled to an edge 502 of the base that is proximate an aperture 504 in the base 500. For example, a first portion 506 of the clamp 210 may be coupled (e.g., fastened, etc.) to a second portion 508 of the clamp 210. The clamp 210 may be securely positioned when the edge 502 of the base 500 is engaged by the first portion 506 and the second portion 508. By coupling to the edge 502, the clamp 210 may be rotated to adjust the position of the electronic device. For example, the clamp 210 may be rotate to enable testing of the robustness of the connection port 104 when the cable connector 108 is impacted at different locations (based on the rotation of the clamp). The base 500 may include features to enable translation in two or more of axes x, y, and z, shown via a reference coordinate system depicted in FIG. 5. For example, the base 500 may clamp to the platform 206, which enables adjustment in the x-axis and the y-axis. The electronic device may be adjusted in the clamp to move the electronic device (and thus the cable connection 108) in along the z-axis. However, the base 500 may also be movable along the z-axis. Movement of the base 500 may be caused by actuators, motors, and/or other devices and may be under control of the controller 116 and/or the integrated controller 118. One example of a motor that may be used for this purpose, or for other purposes as discussed throughout this disclosure, includes use of a stepper motor, which may allow controlled incremental movement of components of the test fixture 200 or other test fixtures described herein.

Figure 6A:
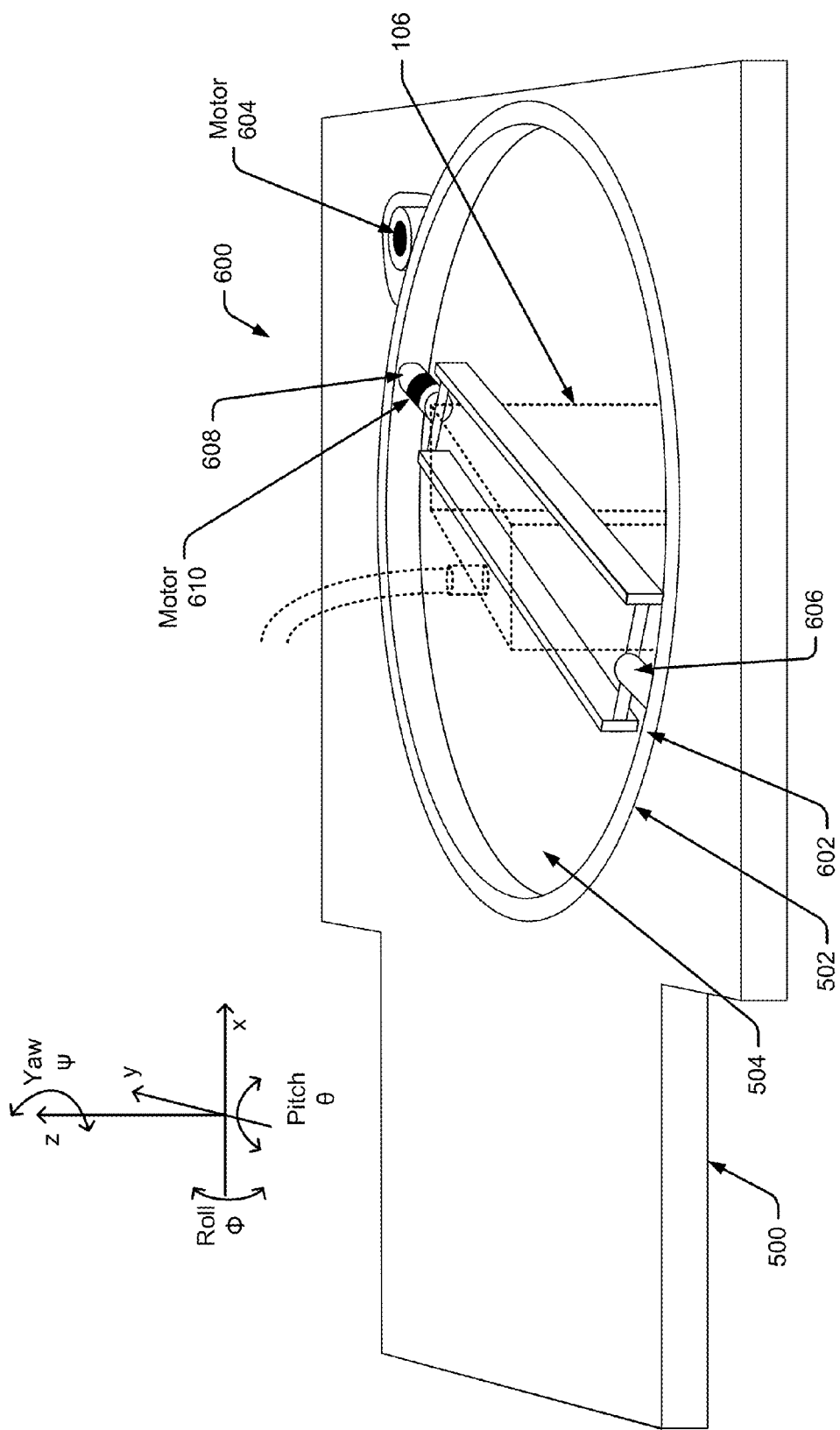
FIGS. 6A and 6B are isometric views of illustrative movable clamping assemblies that can reposition a device by actuation of one or more motors.

FIG. 6A is an isometric view of an illustrative movable clamping assembly 600 that can rotate and reposition an electronic device. In some embodiments, the movement/repositioning may be caused by actuation of one or more motors. The clamping assembly 600 may enable rotation of the clamp 210 with respect to one or more of the Euler angles. The Euler angles are shown in a reference coordinate system in FIG. 6A, which devices roll Φ, pitch θ, and yaw Ψ.

In some embodiments, the clamp 210 may rotate about the z-axis, and thus cause yaw. The clamp 210 may be coupled to an inner ring 602 that rotates about the edge 502 of the aperture 504 of the base 500. A motor 604 may drive the inner ring 602, and thus cause rotation of the clamp 210 with respect to the base 500.

In various embodiments, the clamp 210 may rotate about the x-axis (causing roll) and/or the y-axis (causing pitch). The clamp 210 may be coupled to axles 606 and 608. At least one of the axles may include a motor 610, such as the axle 608. The motor 610 may cause rotation of the clamp 210 via the axles 606 and 608. The controller 116 and/or the integrated controller 118 may control the motor 604 and/or the motor 610. In some embodiments, the axles 606 and 608 and/or the ring 602 may be secured (fixed, not capable of rotation) via set screws, actuators, torque imposed by a motor, and/or similar apparatuses.

Figure 6B:
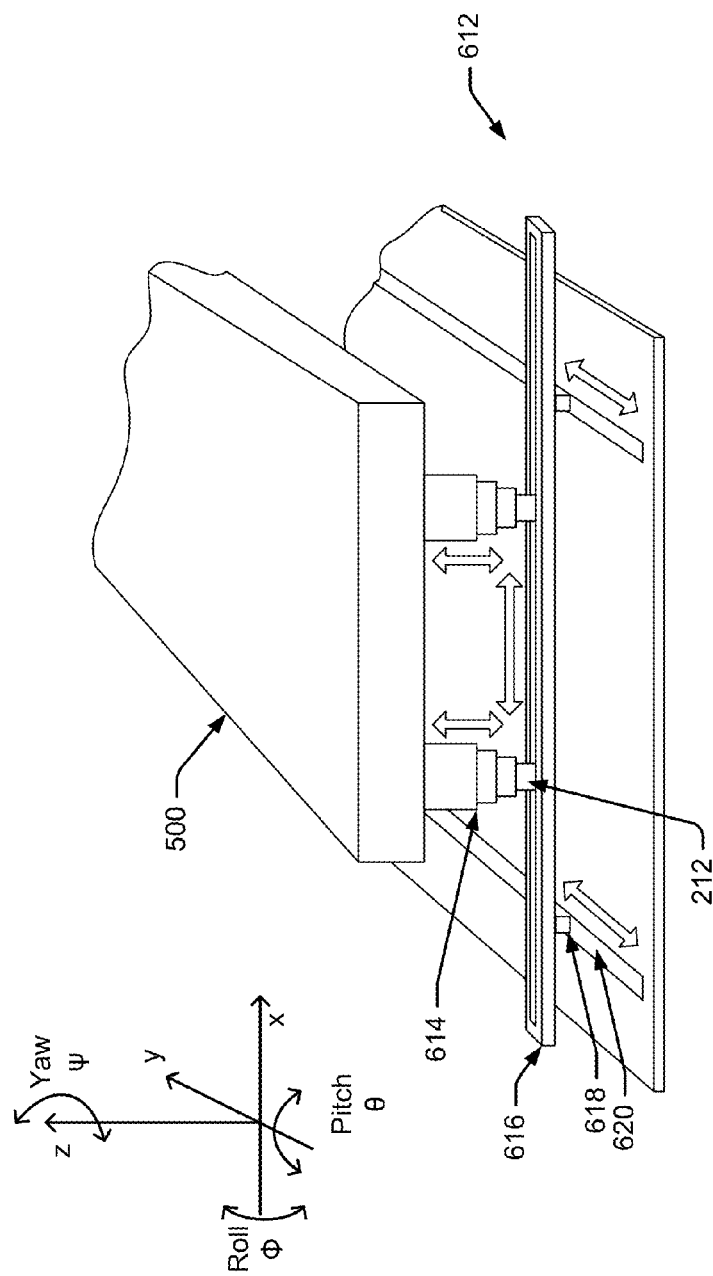

FIG. 6B is an isometric view of an illustrative movable clamping assembly 612 that can translate and reposition an electronic device. In some embodiments, the movement/repositioning may be caused by actuation of one or more motors that translate the base 500 along one or more axes. The axes x, y, and z are shown in a reference coordinate system in FIG. 6B. In various embodiments, the feet 212 may be coupled to legs 614 that are adjustable in length by activation of one or more motors, such as by performing a telescoping operation under control of the one or more motors. Thus, adjustment of the length of the legs 614 may cause translation of the base 500 along the z-axis. The feet 212 may be movable by one or more motors along a first track 616, which may cause translation of the base 500 along the x-axis. The first track 616 may include track feet 618. The track feet 618 may be movable along a second track 620, in response to control of one or more motors, to cause translation of the base 500 along the y-axis. The second track 620 may be included in the platform 206 or another part of the test fixture 200. Other structures may be used to cause the translation of the base 500 in one or more of the axes of x, y, and z.

FIG. 7 is side elevation view of an illustrative test fixture 700 that includes a drive motor 702 configured to reposition the pendulum 112 prior to a release of the pendulum. Thus, the drive motor 702 may move the pendulum 112 from the second position 304 to the first position 302 as shown with reference to FIG. 3.

The drive motor 702 may be an electric motor (e.g., a stepper motor, brushless electric motor, etc) that can engage a drive wheel 704 that is fixedly coupled to the axle 204. When the drive motor 702 is activated, the drive motor 702 may cause the drive wheel 704 to rotate, in turn, rotating the axle 204 and causing the pendulum 112 to rotate toward the first position 302 (or another position or angle). In some embodiments, the drive motor 702 may include friction features that engage the drive wheel, such as a drive belt, gear teeth, and/or other friction features.

At some point in time after the drive motor 702 positions the pendulum 112 at the first position 302 (or other desired position), the drive motor 702 may be moved so that the drive motor 702 disengages the drive wheel 704, allowing the drive wheel 704 to rotate without also causing rotation of the drive motor 702. In some embodiments, the drive motor 702 may be coupled to an arm 706 that may enable translation of the drive motor 702 between an engaged position 708, where the drive motor 702 is engaged with the drive wheel 704, and an unengaged position 710, where the drive motor 702 is not engaged with the drive wheel 704. In various embodiments, a translator 712 may cause the drive motor 702 to move between the engaged position 708 and the unengaged position 710. For example, the translator 712 may be configured as a motor that rotates the arm 706, thus causing the translation of the drive motor 702 or the translator 712 may directly move the drive motor 702 when the translator 712 is implemented as an actuator. The drive motor 702 may follow a path 714 during the translation. The path 714 may include a slot or other feature that at least partially restrains movement of the drive motor 702.

As shown in FIG. 7, a main operation of the drive motor 702 is to rotate the drive wheel 704 in a counterclockwise direction, which raises the pendulum 112 and creates potential energy via the weight 114. Once the pendulum 112 reaches the first position 302, the pendulum 112 may be restrained by a trigger mechanism. In some embodiments, the translator 712 may act as the trigger mechanism. For example, when engagement of the drive motor 702 with the drive wheel 704 is used to restrain the pendulum 112 in the first position 302, then the disengagement of the drive motor 702 (caused by the translator 712) may free the pendulum 112 to return to the second position 304, and thus cause a test cycle where the weight 114 impacts the cable connector 108. However, other trigger mechanisms are described below with reference to FIGS. 9, 9A, and 9B.

Figure 8:
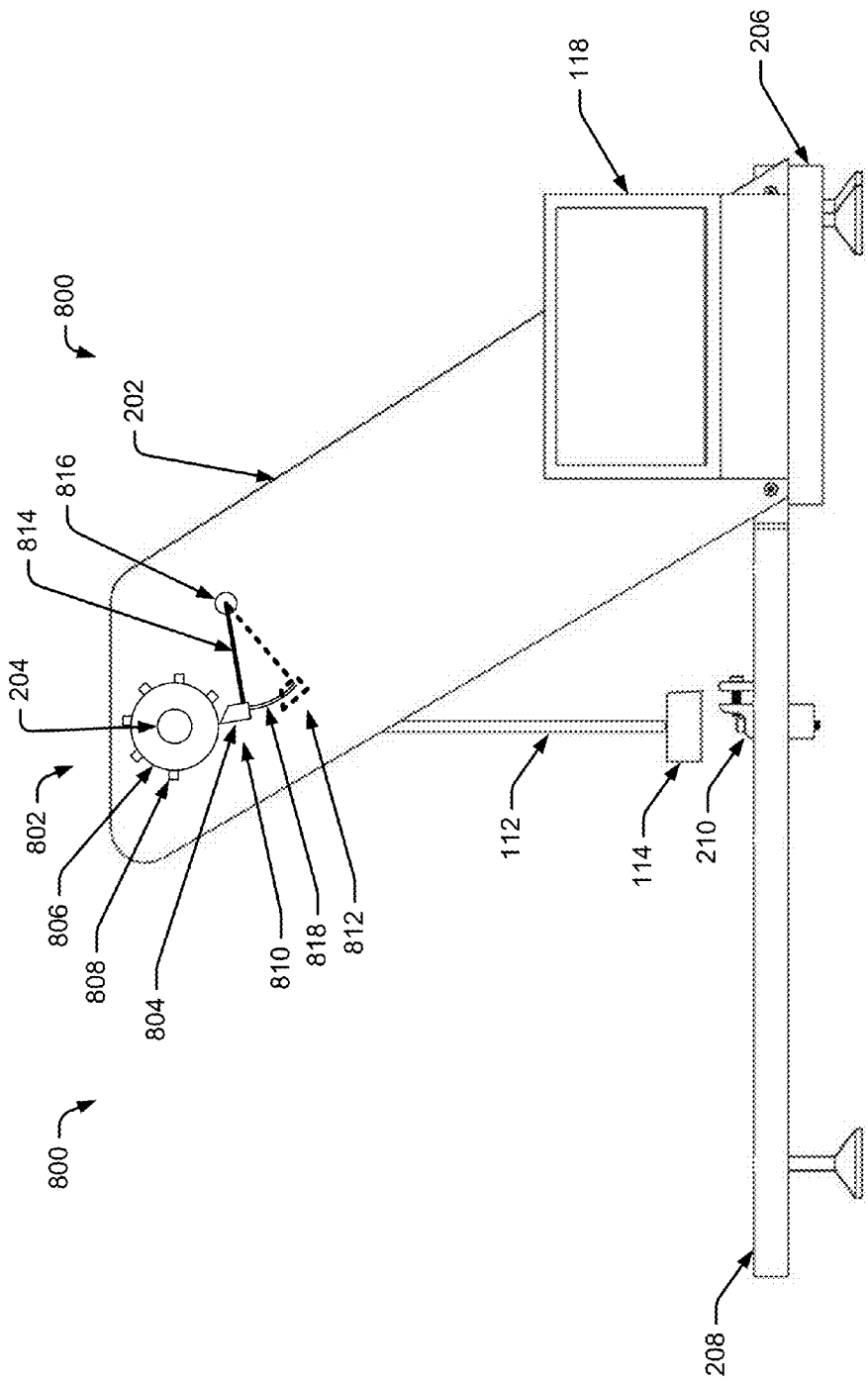
FIG. 8 is side elevation view of the illustrative test fixture that includes a trigger mechanism configured to restrain the pendulum prior to a test using a ratchet mechanism, and to release the pendulum to initiate a test.

FIG. 8 is side elevation view of an illustrative test fixture 800 that includes a trigger mechanism 802 configured to restrain the pendulum 112 prior to a test using a ratchet mechanism, and to release the pendulum 112 to initiate a test. The trigger mechanism 802 may be used with the drive motor 702 discussed with reference to FIG. 7. However, the trigger mechanism 802 may also be used without the drive motor 702, such as when other processes are used to move the pendulum 204 to the first position 302 (e.g., moved by a user, moved by a pulley system, etc.). For example, the pendulum 204 may be moved by a mechanical latch or cable wound by a spool.

The trigger mechanism 802 (which incorporates a ratchet mechanism) includes a stopper 804 that contacts an axle wheel 806 coupled to the axle 204. The axle wheel 806 includes features 808 (e.g., teeth, extrusions, etc.) located at positions that correspond to positions of the pendulum 112. As the pendulum 112 is raised from the second position 304 to the first position 302 (as shown in FIG. 3), the axle wheel 806 rotates in a clockwise direction (from the perspective shown in FIG. 8). The stopper 804, when engaged with the axle wheel 806 in an engaged position 810, permits the axle wheel 806 to only fully rotate in the clockwise direction. The stopper 804 includes an angled edge that allows passage of the features 808 when the axle wheel 806 rotates in the clockwise direction. The stopper 804 includes a non-angled edge opposite the angled edge that prevents the axle wheel 806 from fully rotating in the counterclockwise direction, thereby acting as a ratchet mechanism by restraining counterclockwise rotate of the axle wheel 806. The features 808 may be placed in predetermined locations on the axle wheel 806. The predetermined locations may correspond to various desired positions of the pendulum 112. Thus, one of the features 808 may correspond to restraining the pendulum 112 in the first position 302.

To release the pendulum 112 and initiate a test that involves the weight 114 impacting the cable connector 108, the stopper 804 may translate from the engaged position 810 to an unengaged position 812 that allows the axle wheel 806 to rotate freely in the counterclockwise direction (from the perspective shown in FIG. 8). In some embodiments, the stopper 804 may be coupled to an arm 814 that may enable translation of the stopper 804 between the engaged position 810 and the unengaged position 812. In various embodiments, a translator 816 may cause the stopper 804 to move between the engaged position 810 and the unengaged position 812. For example, the translator 816 may be configured as a motor that rotates the arm 814, thus causing the translation of the stopper 804 or the translator 816 may directly move the stopper 804 when the translator 816 is implemented as an actuator. The stopper 804 may follow a path 818 during the translation. The path 818 may include a slot or other feature that at least partially restrains movement of the stopper 804. When the stopper 804 is in the engaged position, the stopper 804 may be biased against the axle wheel 806 by a spring, by the translator 816, or by another biasing device.

Once the pendulum 112 reaches a desired position, the stopper 804 engages one of the features 808 causing the pendulum 112 to maintain a position where the weight 114 includes potential energy, such as the first position 302. The translator 816 may act as the trigger mechanism by causing the stopper 804 to translate from the engaged position 810 to the unengaged position 812, thereby releasing the pendulum 112.

Figure 9B:
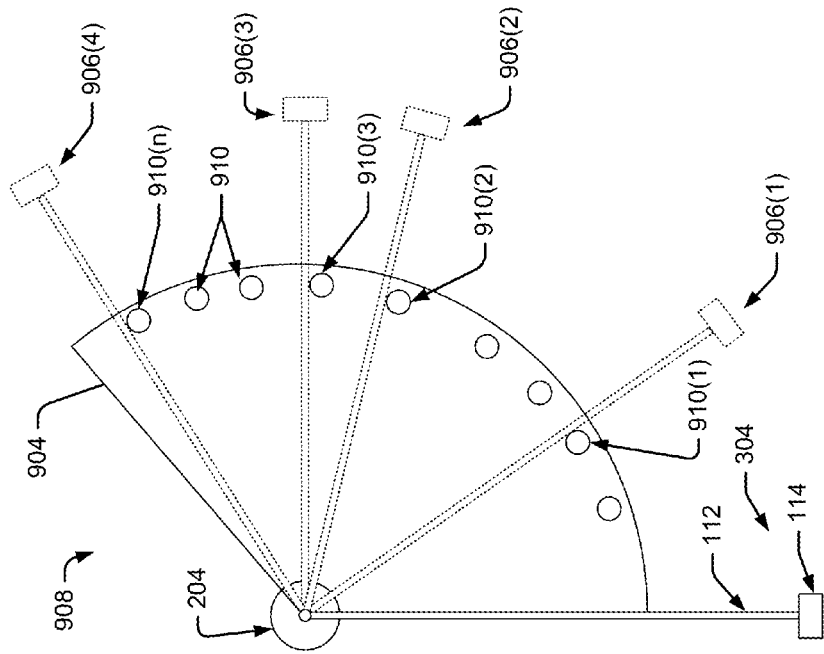
FIGS. 9A and 9B are side elevation views of trigger mechanisms configured to restrain the pendulum prior to a test, and to release the pendulum to initiate a test.
Figure 9A:
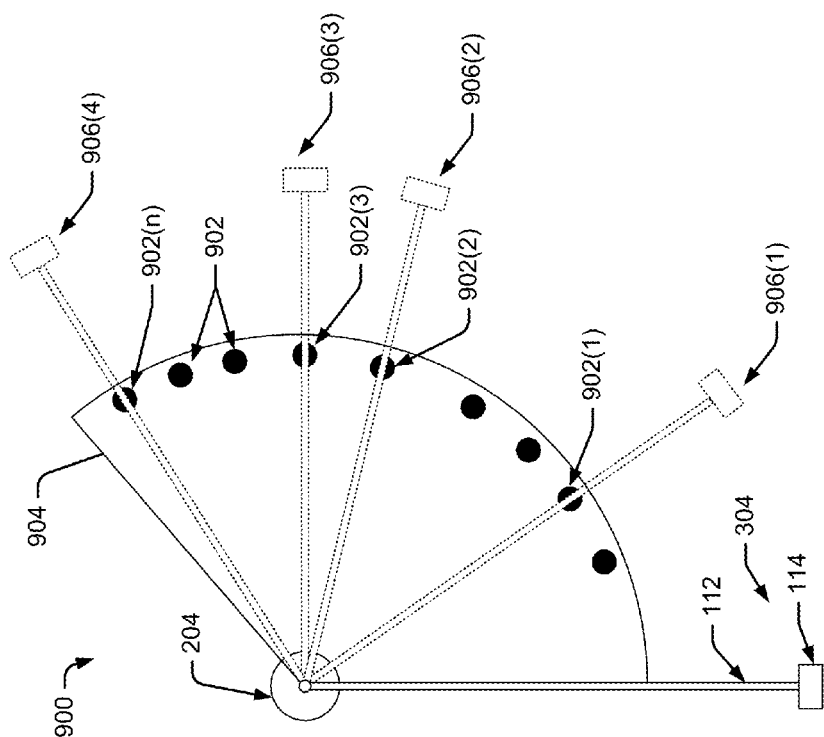

FIGS. 9A and 9B are side elevation views of various trigger mechanisms configured to restrain the pendulum 112 prior to a test, and to release the pendulum to initiate a test.

FIG. 9A shows an illustrative trigger mechanism 900. The trigger mechanism 900 includes a plurality of magnets 902 that are selectively powered by the controller 116 and/or the integrated controller 118. When powered, the magnets may include a magnetic field that may restrain the pendulum 112 in a position, such as the first position 302 shown in FIG. 3. The plurality of magnets 902 may be located along a frame 904 in positions that cause the pendulum 112 to be restrained at known locations or angles (e.g., at the first position 302, etc.). The frame 904 may be situated at least partially around the axle 204. As an example, a first magnet 902(1) may be located in a position that corresponds to a first position 906(1) of the pendulum 112. The pendulum 112 is shown with dashed lines at each of positions 906(1), 906(2), 906(3), ..., 906(n) for illustrative purposes. Magnets 902(1), 902(2), 902(3), ..., 902(n) cause the pendulum 112 to be restrained at the positions 906(1), 906(2), 906(3), ..., 906(n), respectively. When the magnet or magnets are powered off (reversed in polarity, etc.) or the magnetic field is otherwise removed or reduced, then the pendulum 112 may be released (triggered) to initiate a test where the pendulum 112 swings back to the second position 304.

FIG. 9B shows a trigger mechanism 908 that also includes the frame 904. However, the trigger mechanism 908 may include features 910, such as extruded pins or other features that restrain the pendulum 112 in various positions. The features 910 may support the pendulum 112 and prevent the pendulum from releasing the potential energy of the weight 114 that is associated with a position. Features 910(1), 910(2), 910(3), ..., 910(n) cause the pendulum 112 to be restrained at the positions 906(1), 906(2), 906(3), ..., 906(n), respectively. When the features 910 are moved away from the pendulum 112 causing the features to lose contact with the pendulum 112, then the pendulum 112 may be released to initiate a test where the pendulum swings back to the second position 304. The features 910 may be moved away from the pendulum 112 by a motor, actuator, or other mechanism. For example an actuator or motor may move the frame 904 between an unengaged position, where the pendulum 112 can move, and an engaged position, where the pendulum 112 is restrained by at least one of the features 910.

Illustrative Operation

Figure 10:
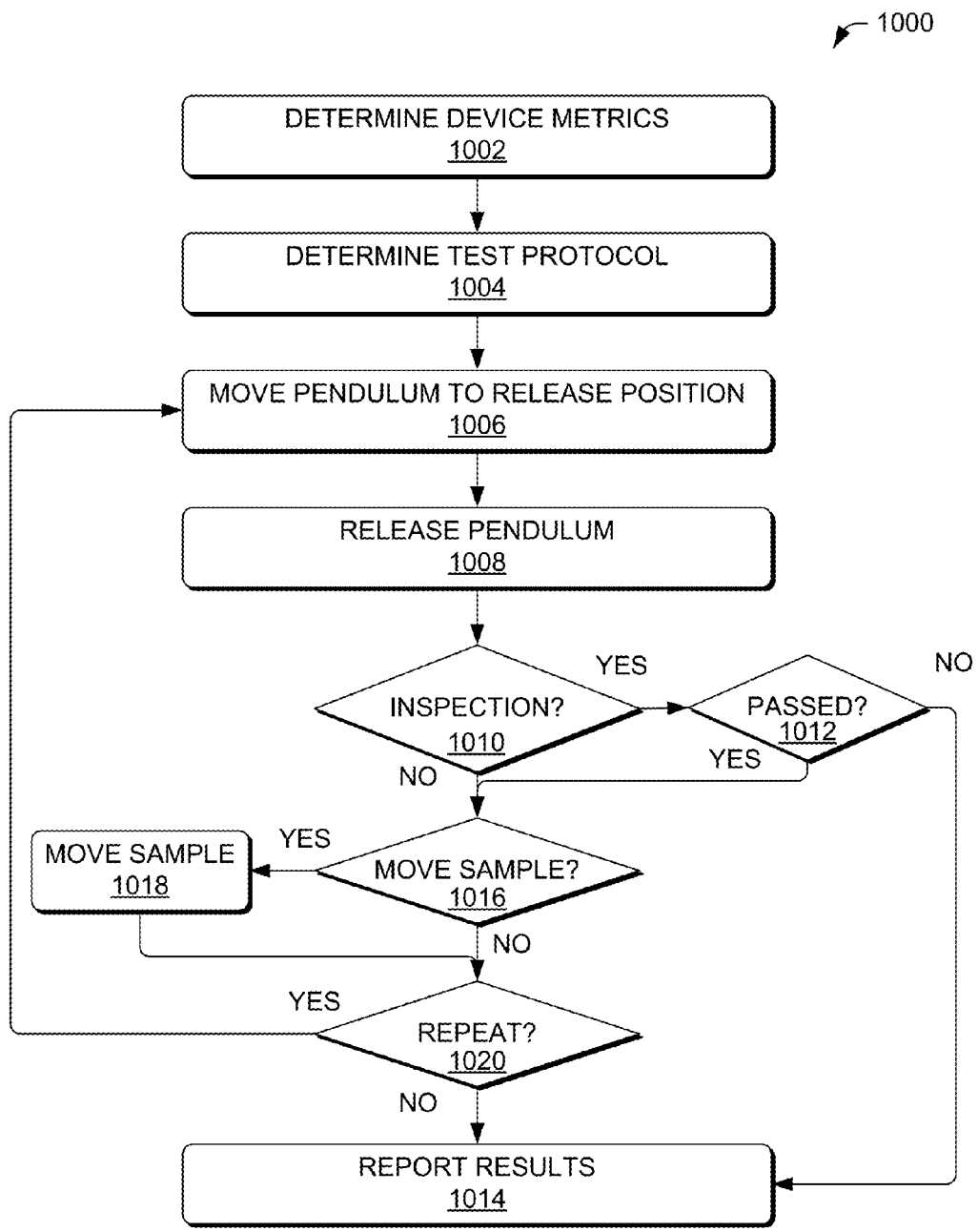
FIG. 10 is a flow diagram of an illustrative process to perform a reliability test for connection ports and/or cable connectors.

FIG. 10 is a flow diagram of an illustrative process 1000 to perform a reliability test for connection ports and/or cable connectors. The process 1000 is illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes. The process 1000 may be implemented using the environment 100 or the process may be implemented in other environments.

At 1002, the controller (e.g., the controller 116 and/or the integrated controller 118) may determine device metrics. For example, the device metrics may include a weight of the electronic device 106, a simulated drop distance, dimensions of the electronic device, and so forth.

At 1004, the controller may determine a test protocol for testing the device. The test protocol may include a number cycles in a test, one or more positions of the electronic device 106 in the clamp, a position associated with each test cycle, test passage criteria, test termination criteria (e.g., broken connection port, etc.), and/or other test parameters.

At 1006, the controller or a user may move the pendulum to the release position (e.g., the first position 302). For example, the controller may power the drive motor 702 to move the pendulum to the release position. At the release position, the pendulum 112 may be restrained by a trigger mechanism, such as the ratchet mechanism described with reference to FIG. 8, the drive motor 702 while engaged with the drive wheel 704 shown in FIG. 7, by the trigger mechanisms 900 or 908, and/or by other trigger mechanisms.

At 1008, the controller may cause the trigger mechanism to release the pendulum 112. By releasing the pendulum 112, gravity releases the potential energy of the weight 114 and causes the pendulum 112 and the weight 114 to travel to the second position 304 and impact the cable connector 108 engaged to the connection port 104.

At 1010, the controller may inspect operation and/or integrity of the cable connector 108 and/or the connection port 104. For example, the operation may be tested by determine whether the cable connector 108 can provide data, power, etc. to the electronic device 106 through the connection port 104. The integrity may be tested by inspecting imagery of the respective parts. When the inspection is to occur (following a "yes" route from the decision operation 1010), then the controller (or possibly a human) may determine whether the test was passed at a decision operation 1012 (e.g., operation confirmed, no damage to device, minimal damage, etc.). When the controller determines that the inspection did not pass (following a "no" route from the decision operation 1012), then the test may end and the controller may report results of the test at 1014.

When no inspection occurs (following a "no" route from the decision operation 1010) or when the inspection is passed (following a "yes" route from the decision operation 1012), then the process 1000 may continue at a decision operation 1016. At the decision operation 1016, the controller may determine whether to move and/or reposition the electronic device 106 (the sample). The controller may cause motors to rotate or translate the clamp (as discussed with reference to FIG. 6A). The movement may be to reposition the electronic device 106 to a same position as used in the previous test (assuming the electronic device may move when the weight 114 strikes the cable connector 108). The movement may be to position the electronic device 106 in a new position for the next cycle, such as by rotating the electronic device a predetermined amount, etc. When the electronic device is to be moved (repositioned) (following a "yes" route from the decision operation 1016), then the electronic device is moved at 1018.

When no movement or repositioning occurs (following a "no" route from the decision operation 1016) or following the movement or repositioning at the operation 1018, then the process 1000 may continue at a decision operation 1020. At the decision operation 1020, the controller may determine whether to repeat the test (and thus reposition the pendulum at the operation 1006). The controller may repeat the test when additional test cycles need to be run or for other reasons. When no additional tests are to be performed (following a "no" route from the decision operation 1020), the process 1000 may advance to the operation 1014 and report the results of the test.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A testing device to test a robustness of at least one of a connection port of an electronic device or a cable connector while the cable connector is coupled to the connection port, the testing device comprising:
   a clamp to securely position the electronic device;
   a pendulum including an arm coupled to an axle, and a weight coupled to a distal end of the arm;
   a trigger mechanism to selectively restrain the pendulum at a first angle where the weight has potential energy, and to selectively release the pendulum and the potential energy and allow the pendulum to rotate to a second angle where the weight impacts the cable connector while the cable connector is coupled to the connection port of the electronic device, the trigger mechanism causing the selective release after displacement of a restraint or adjusting a magnetic field of a magnet that restrained the pendulum;
   a frame to securely position the clamp, the trigger mechanism, and the axle while allowing the axle and the pendulum to controllably rotate between the first angle and the second angle, wherein the clamp allows rotation of the electronic device with respect to the frame;
   a motor coupled to the clamp or the frame to cause the rotation of the electronic device with respect to the frame; and
   a controller coupled to at least the trigger mechanism, the controller to at least activate the trigger mechanism to cause the selective release of the pendulum, wherein the controller selectively operates the motor to position the connection port and the cable connector in a path of travel of the pendulum, wherein the controller comprises a data input module coupled to a cable, wherein the cable is coupled to the cable connector, and wherein the data input module is configured to determine that the cable connector and the connection port perform a function following an impact of the weight against the cable connector, the function including transmission of at least one of data, audio, video, or power between the cable connector and the connection port.

2. The testing device as recited in claim 1, further comprising a drive motor coupled to the frame, the drive motor to engage the axle and to reposition the pendulum from the second angle to the first angle.

3. The testing device as recited in claim 2, where the drive motor is the restraint that is displaced by the trigger mechanism, and wherein the drive motor is further configured to:
   maintain the pendulum at the first angle until the trigger mechanism displaces the drive motor; and
   disengage the axle or the pendulum to enable the pendulum to freely rotate to the second angle.

4. The testing device as recited in claim 2, wherein the controller further operates to perform repetitive testing of two or more test cycles, and wherein a test cycle includes a release of the pendulum, by the trigger mechanism, from the first angle and the reposition of the pendulum, by the drive motor, from the second angle to the first angle.

5. An apparatus comprising:
   a clamp to securely position an electronic device;
   a pendulum including an arm coupled to an axle, and a weight coupled to a distal end of the arm;
   a trigger mechanism to selectively restrain the pendulum at a first angle where the weight has potential energy, and to selectively release the pendulum and the potential energy and allow the pendulum to rotate to a second angle where the weight impacts a cable connector while the cable connector is coupled to a connection port of the electronic device;
   a frame to securely position the clamp, the trigger mechanism, and the axle while allowing the axle and the pendulum to controllably rotate between the first angle and the second angle; and
   a controller coupled to at least the trigger mechanism, the controller to at least activate the trigger mechanism to release the pendulum, wherein the controller includes a data input module coupled to the cable connector, the controller to determine at least whether the cable connector and the connection port perform a function following the impact of the weight against the cable connector, the function including transmission of at least one of data, audio, video, or power between the cable connector and the connection port.

6. The apparatus as recited in claim 5, wherein the trigger mechanism includes a ratchet mechanism that is coupled to the frame, the ratchet mechanism operating in an engaged position where a stopper engages an axle wheel that includes teeth, the ratchet mechanism allowing rotation of the axle in one direction while in the engaged position, the stopper engaging the teeth on the axle wheel to prevent the rotation of the axle in an opposite direction and thereby restrain the pendulum at the first angle, the trigger mechanism to cause the stopper to translate to a unengaged position where the stopper is disengaged from the axle wheel and the teeth thereby allowing the pendulum to rotate from the first angle to the second angle.

7. The apparatus as recited in claim 6, the controller configured to:
   activate the trigger mechanism to move the stopper to the unengaged position to release the pendulum and the potential energy; and
   activate the trigger mechanism to move the ratchet mechanism back to the engaged position after the pendulum has rotated from the first angle to the second angle.

8. The apparatus as recited in claim 5, further comprising a drive motor coupled to the frame, the drive motor to engage the axle, the drive motor configured to at least reposition the pendulum from the second angle to the first angle, and wherein the controller selectively operates the motor to cause the motor to reposition the pendulum.

9. The apparatus as recited in claim 8, wherein the controller further operates to perform repetitive testing of two or more test cycles, and wherein a test cycle includes a release of the pendulum, by the trigger mechanism, from the first angle and the reposition of the pendulum, by the drive motor, from the second angle to the first angle.

10. The apparatus as recited in claim 5, wherein the clamp allows rotation with respect to the frame, and further comprising a motor coupled to the clamp or the frame to cause the rotation, and wherein the controller selectively operates the motor to cause the rotation of the clamp and position the connection port and the cable connector in a path of travel of the pendulum.

11. The apparatus as recited in claim 5, further comprising causing, by the controller, rotation of the clamp to reposition the connection port and the cable connector in a path of travel of the pendulum after the weight impacts the cable connector.

12. The apparatus as recited in claim 5, further comprising a camera to record imagery of at least the cable connector or the connection port, and wherein the controller operates the camera to cause recording of the imagery.

13. The apparatus as recited in claim 12, wherein the controller is a general purpose computing device, and wherein the controller analyzes the imagery to determine whether the cable connector or the connection port has experienced a physical deterioration.

14. A method, comprising:
securing a device in a test fixture;
positioning the device to align a cable connector, coupled to a connection port of the device, along a path of travel of a weight that is coupled to a pendulum;
positioning, using a drive motor under control of a controller, the pendulum at a first angle relative to a directional pull of gravity, the pendulum and the weight having potential energy at the first angle;
releasing, using the controller, the pendulum that includes the weight, the releasing to allow the pendulum to release the potential energy by moving from a first position to a second position; and
determining at least one of:
whether the cable connector and the connection port perform a function following an impact of the weight against the cable connector, wherein the function includes one of: transmitting data, audio, or power to the connection port; or
whether the cable connector or the connection port experience a physical deterioration following the impact of the weight against the cable connector.

15. The method as recited in claim 14, wherein the determining is performed at least in part by the controller that is coupled to at least one of a camera or the cable connector.

16. The method as recited in claim 14, wherein the releasing is performed by a trigger mechanism, under control of the controller, the trigger mechanism causing a selective release after displacement of a restraint or adjustment of a magnetic field of a magnet that restrained the pendulum.

17. The method as recited in claim 14, further comprising performing cycle tests that include repositioning the pendulum at the first angle and releasing the pendulum until the cable connector and the connection port fail to perform the function or until the pendulum is released a threshold number of times.

18. A system comprising:
a device tester, including:
a clamp to securely position an electronic device;
a pendulum including an arm coupled to an axle, and a weight coupled to a distal end of the arm;
a trigger mechanism to selectively engage a restraint to restrain the pendulum at a first angle where the weight has potential energy, and to selectively release the restraint to release the pendulum and the potential energy and allow the pendulum to rotate to a second angle where the weight impacts a cable connector while the cable connector is coupled to a connection port of the electronic device; and
a frame to securely position the clamp, the trigger mechanism, and the axle while allowing the axle and the pendulum to controllably rotate between the first angle and the second angle;
a motor coupled to the clamp or the frame to cause a rotation of the electronic device with respect to the frame; and
a computing device to at least partly control operation of the device tester, wherein the computing device selectively operates the motor to cause the rotation of the electronic device to position the connection port or the cable connector in a path of travel of the pendulum.

19. The system as recited in claim 18, wherein the restraint includes at least two positions for restraining the pendulum, each position having an associated amount of potential energy.

20. The system as recited in claim 18, wherein the clamp is rotatable along at least two axes with respect to the frame.

21. The system as recited in claim 18, wherein the clamp is coupled to a base that is coupled to the frame, and wherein a position of the base is movable with respect to the frame.

22. The testing device as recited in claim 1, the controller further coupled to a camera to record imagery of at least the cable connector or the connection port, and wherein the controller operates the camera to cause recording of the imagery, and wherein the controller analyzes the imagery to determine whether the cable connector or the connection port has experienced a physical deterioration.

23. The apparatus as recited in claim 5, wherein the controller is configured to position the electronic device to a same position used in a first test and a second test.

24. The method as recited in claim 14, further comprising repositioning the device to align the cable connector, coupled to the connection port of the device, along the path of travel of the weight that is coupled to the pendulum following a first test cycle.

* * * * *